United States Patent
Hilliard, Jr. et al.

(10) Patent No.: US 10,933,000 B2
(45) Date of Patent: Mar. 2, 2021

(54) ALUMINUM-FREE ANTIPERSPIRANT / DEODORANT COMPOSITIONS

(71) Applicant: Colgate-Palmolive Company, New York, NY (US)

(72) Inventors: Peter Hilliard, Jr., Far Hills, NJ (US); Sharon Kennedy, Randallstown, MD (US); Darrick Carlone, New Vernon, NJ (US); Cristina Bielli, Hillsborough, NJ (US); Richard Adams, South Orange, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 16/468,342

(22) PCT Filed: Dec. 7, 2017

(86) PCT No.: PCT/US2017/064988
§ 371 (c)(1),
(2) Date: Jun. 11, 2019

(87) PCT Pub. No.: WO2018/111664
PCT Pub. Date: Jun. 21, 2018

(65) Prior Publication Data
US 2019/0298625 A1    Oct. 3, 2019

Related U.S. Application Data

(60) Provisional application No. 62/434,214, filed on Dec. 14, 2016.

(51) Int. Cl.
| | | |
|---|---|---|
| *A61K 8/02* | (2006.01) | |
| *A61K 8/04* | (2006.01) | |
| *A61K 8/27* | (2006.01) | |
| *A61K 8/34* | (2006.01) | |
| *A61K 8/36* | (2006.01) | |
| *A61K 8/81* | (2006.01) | |
| *A61Q 15/00* | (2006.01) | |

(52) U.S. Cl.
CPC .............. *A61K 8/27* (2013.01); *A61K 8/0229* (2013.01); *A61K 8/042* (2013.01); *A61K 8/345* (2013.01); *A61K 8/361* (2013.01); *A61K 8/8164* (2013.01); *A61K 8/8182* (2013.01); *A61Q 15/00* (2013.01); *A61K 2800/30* (2013.01)

(58) Field of Classification Search
CPC ... A61K 8/02; A61K 8/04; A61K 8/27; A61K 8/34; A61K 8/36; A61K 8/81; A61Q 15/00
See application file for complete search history.

(56) References Cited

U.S. PATENT DOCUMENTS

| | | |
|---|---|---|
| 3,721,693 A | 3/1973 | Fein et al. |
| 4,322,400 A | 3/1982 | Yuhas |
| 4,722,835 A | 2/1988 | Schamper et al. |
| 4,777,034 A | 10/1988 | Olivier |
| 4,814,164 A | 3/1989 | Barth et al. |
| 5,258,174 A | 11/1993 | Schebece |
| 5,512,274 A | 4/1996 | Phinney |
| 6,358,499 B2 | 3/2002 | Hall-Puzio et al. |
| 6,538,499 B1 | 3/2003 | Lu |
| 6,844,409 B2 | 1/2005 | Klug et al. |
| 7,807,189 B2 | 10/2010 | Hassan et al. |
| 8,563,754 B2 | 10/2013 | Orlow et al. |
| 9,314,412 B2 | 4/2016 | Phinney |
| 9,827,177 B2 | 11/2017 | Yuan et al. |
| 2006/0045860 A1 | 3/2006 | Gupta |
| 2011/0030083 A1 | 2/2011 | Fowler |
| 2011/0300083 A1 | 12/2011 | Yontz et al. |
| 2014/0242015 A1* | 8/2014 | Fares ................. A61K 8/19 424/67 |

FOREIGN PATENT DOCUMENTS

| | | |
|---|---|---|
| JP | S64-8971 A | 1/1989 |
| JP | H05-10951 B2 | 2/1993 |
| JP | H06-114095 A | 4/1994 |
| WO | 1999/059539 | 11/1999 |
| WO | 2000/049996 | 8/2000 |
| WO | 2006/023882 | 3/2006 |
| WO | 2013/052454 | 4/2013 |
| WO | 2016/098045 | 6/2016 |

OTHER PUBLICATIONS

International Search Report and Written Opinion of the International Searching Authority in International Application No. PCT/US2017/064988, dated Mar. 27, 2018.

* cited by examiner

*Primary Examiner* — Zohreh A Fay

(57) ABSTRACT

An aluminum-free antiperspirant/deodorant composition in the form of stick, cream, or flowable gel includes a carrier that includes a polyhydric alcohol or is a mixture of a polyhydric alcohol and water; a thickening agent including a $C_{14-22}$ fatty acid salt; and an antiperspirant active and optionally a film-forming polymer dispersed in the carrier. The antiperspirant active is primarily a zinc-based antiperspirant active.

15 Claims, 4 Drawing Sheets

Before · After

Before · After

ALUMINUM-FREE ANTIPERSPIRANT / DEODORANT COMPOSITIONS

BACKGROUND

Antiperspirant/deodorant compositions are used to reduce the perspiration in an axillary (underarm) region and/or to kill bacteria in this region to reduce or eliminate body odor caused by bacterial growth in this region. Antiperspirants/deodorants can be provided in many forms, such as a roll on, a gel, or as a solid stick. Stick antiperspirant/deodorant applicators are essentially made of a solid or semi-solid material (i.e., a base composition that is firm to the touch) impregnated with ingredients that function to reduce perspiration, kill bacteria or limit their growth by reducing the moist climate in which bacteria thrive, fragrances, stabilizers, moisturizers, etc. To use the stick applicator, the user swipes the stick applicator in the armpit one or more times thereby coating the underarm with a thin layer of the antiperspirant/deodorant material. As would be expected, there are characteristics that make some carrier materials superior to others. For example, product hardness, moisture content, stickiness, oiliness, wetness, ease by which the antiperspirant/deodorant material goes on to the underarm (payout) and ease of application (e.g., how much pressure does the user have to use to deposit the required amount of deodorant material to the underarm referred to herein as "glide"), the ability of the deodorant material to stay on the underarm skin and hair and resist coming off (retention), visibility of deodorant residue on skin and clothing (visible residue), staining of clothing, irritation and inflammation of the skin, flow resistant to body heat (i.e., the deodorant composition material does not "drip" or "run" appreciably after application), etc.

Various metallic salts, for example, of zinc, iron and aluminum, have been used as antiperspirant actives, with chlorohydrates and chlorides of aluminum, and aluminum and zirconium being the most commonly used antiperspirant active. However, there is a growing desire to replace these salts with other active metal salts. Zinc, which has antibacterial property, has been explored as a possible candidate to replace aluminum. However, Phinney in U.S. Pat. No. 5,512,274 reported that zinc salts precipitate as hydroxides in the range of pH of 6.5 to 8.0, and have been shown to behave erratically, being effective as an antiperspirant only for very irregular periods of time, which makes them undependable. The sporadic efficacy of zinc salts was speculated to be due to various factors, such as lack of hydrolysis conversion to relatively inactive carbonate or oxide, or some other factor or combination of factors.

Yuan and Pan, in U.S. patent publication no. 2015/0313821, reported that zinc oxide is weakly soluble at low pH. However, due to human perspiration having a pH of 5-6, the perspiration can reduce the levels of precipitation of the zinc oxide compared to precipitation levels at neutral pH. Moreover, the perspiration can gradually dissolve the depositions, reducing the duration of action of the formulation.

Hence, there remains a desire for new antiperspirant/deodorant compositions in the form of liquid (e.g., roll-on), stick, cream, or flowable gel, that provide increased substantivity of zinc on a skin surface with reduced visible residue.

BRIEF SUMMARY

In an aspect, there is an antiperspirant/deodorant composition comprising: a base composition and an antiperspirant active and a film-forming polymer dispersed in the base composition, wherein the base composition comprises a carrier comprising a polyhydric alcohol or a mixture of a polyhydric alcohol and water, wherein the polyhydric alcohol comprises an organic compound containing 2 to 6 carbon atoms and 2 to 6 hydroxy groups; and a thickening agent comprising a $C_{14-22}$ fatty acid salt, wherein the $C_{14-22}$ fatty acid salt comprises at least one of an alkali metal, an alkaline earth metal, a transition metal, or an amine salt of $C_{14-22}$ fatty acid, and wherein the antiperspirant active consists essentially of a zinc-based antiperspirant active.

In an embodiment of the antiperspirant/deodorant composition, the zinc-based antiperspirant active comprises one or more of zinc oxide, zinc hydroxide, zinc hydroxide ions, and zinc ions.

In another embodiment of the antiperspirant/deodorant composition, the antiperspirant/deodorant composition is essentially free of aluminum-based antiperspirant actives and magnesium-based actives.

In another embodiment of the antiperspirant/deodorant composition, the antiperspirant/deodorant composition is includes at least one of aluminum-based antiperspirant actives and magnesium-based actives.

In yet another embodiment of the antiperspirant/deodorant composition, the zinc-based antiperspirant active comprises zinc oxide present in an amount of from 0.5 to 10 weight %, based on the total amount of the antiperspirant/deodorant composition.

In one embodiment of the antiperspirant/deodorant composition, the film-forming polymer comprises at least one of a copolymer of maleic anhydride and methyl vinyl ether crosslinked with 1,9-decadiene, a mixture of polyester-10 and propylene glycol dibenzoate; a mixture of polyester-7 and neopentyl glycol diheptanoate; adipic acid/diglycol crosspolymer; trimethylpentanediol/adipic acid/glycerin crosspolymer; trimethylpentanediol/adipic acid copolymer; capryloyl glycerin/sebacic acid copolymer; and an acyl substituted polyvinylpyrrolidone having an average acyl chain length of 16 to 30 carbon atoms In an embodiment of the antiperspirant/deodorant composition, the film forming polymer comprises a copolymer of maleic anhydride and methyl vinyl ether crosslinked with 1,9-decadiene, present in an amount of 0.1 to 5 weight %, based on the total weight of the antiperspirant/deodorant composition.

In an embodiment of the antiperspirant/deodorant composition, the $C_{14-22}$ fatty acid salt comprises at least one of myristic, palmitic, stearic, behenic, oleic, linoleic, and linolenic acid, and one or more of sodium, potassium, calcium, magnesium, diethylamine, triethyl amine as a counterion.

In another embodiment of the antiperspirant/deodorant composition, the $C_{14-22}$ fatty acid salt comprises a completely or a partially neutralized stearic acid.

In an embodiment of the antiperspirant/deodorant composition, the $C_{14-22}$ fatty acid salt is present in an amount of 0.5 to 8 weight %, based on the total weight of the antiperspirant/deodorant composition.

In an embodiment of the antiperspirant/deodorant composition, the polyhydric alcohol is propylene glycol.

In another embodiment of the antiperspirant/deodorant composition, the polyhydric alcohol is present in an amount of 65 to 95 weight %, based on the total weight of the antiperspirant/deodorant composition.

In one embodiment of the antiperspirant/deodorant composition, the antiperspirant/deodorant composition is in the form of stick, cream, or flowable gel.

In an aspect, there is a method of reducing apparent perspiration comprising applying the antiperspirant/deodorant composition as disclosed hereinabove to an axillary area of a person, wherein the antiperspirant/deodorant composition reduces apparent perspiration.

In another aspect, there is a use of a film-forming polymer in combination with a fatty acid salt and zinc-based antiperspirant active present in the antiperspirant/deodorant composition as disclosed hereinabove for at least one of the following when applied to an axillary area of a person: (a) increase sub stantivity of zinc on a skin surface, (b) enhance resistance to hydrostatic pressure, and (c) reduce visible residue, wherein the film-forming polymer comprises at least one of a Copolymer of maleic anhydride and methyl vinyl ether crosslinked with 1,9-decadiene; a mixture of polyester-7 and neopentyl glycol diheptanoate; adipic acid/diglycol crosspolymer; trimethylpentanediol/adipic acid/glycerin crosspolymer; and trimethylpentanediol/adipic acid copolymer; capryloyl glycerin/sebacic acid copolymer; and an acyl substituted polyvinylpyrrolidone having an average acyl chain length of 16 to 30 carbon atoms.

In another aspect, there is an antiperspirant/deodorant composition comprising:
a) a base composition comprising:
  (i) a carrier consisting essentially of a polyhydric alcohol or a mixture of a polyhydric alcohol and water, wherein the polyhydric alcohol comprises an organic compound containing 2 to 6 carbon atoms and 2 to 6 hydroxy groups;
  (ii) a thickening agent comprising a $C_{14-22}$ fatty acid salt, wherein the $C_{14-22}$ fatty acid salt comprises at least one of an alkali metal, an alkaline earth metal, a transition metal, or an amine salt of $C_{14-22}$ fatty acid;
b) an antiperspirant active consisting essentially of a zinc-based antiperspirant active dispersed in the base composition,
  wherein the antiperspirant/deodorant composition is essentially free of aluminum-based antiperspirant actives and magnesium-based actives.

In one embodiment of the antiperspirant/deodorant composition as disclosed hereinabove, the antiperspirant/deodorant composition is essentially free of morpholine, pyridine, acetic acid, ethylene carbonate, propylene carbonate, N-methyl pyrrolidone, pyrrolidone, butyrolactone, dimethylsulfoxide, dimethyl formamide, 2-ethoxyethanol, caprolactam.

Further areas of applicability of the present disclosure will become apparent from the detailed description provided hereinafter. It should be understood that the detailed description and specific examples, while indicating some preferred aspects of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

Figure 1A:
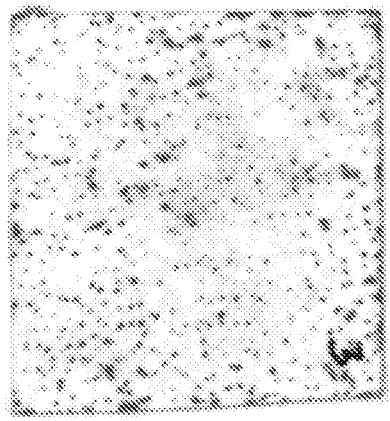
FIG. 1A shows a representative optical image of sweat glands producing perspiration identified by dark spots before and after treatment with an antiperspirant/deodorant composition of the present disclosure comprising 10 weight % zinc oxide.
Figure 1A:
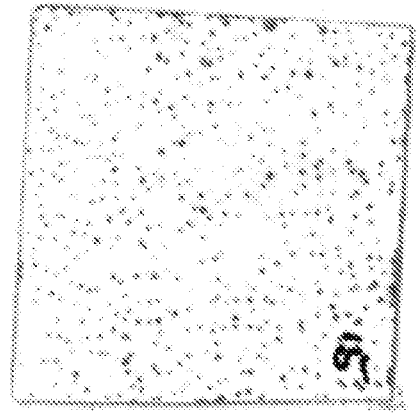

The following description of various preferred aspect(s) is merely exemplary in nature and is in no way intended to limit the invention, its application, or uses.

As used throughout, ranges are used as shorthand for describing each and every value that is within the range as well as the endpoints. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

As used herein, the term "antiperspirant/deodorant compositions" refers to compositions which exhibit at least one of an antiperspirant effect or both an antiperspirant effect and a deodorant effect.

As used herein, the terms "zinc substantivity" and "substantivity of zinc" are used interchangeably and refer to adsorption and retention of zinc, for example in the form of zinc oxide, zinc hydroxide, zinc hydroxide ions, and/or zinc ions, on or within the top layers of a surface, such as a skin surface, and once there, resistance to subsequent removal or rinsing off of the zinc during rinsing procedure performed five times with 100 µl of 0.1 M NaCl solution to simulate perspiration or sweating.

As used herein, the term "zinc sub stantivity enhancer" refers to a film-forming polymer that when used in a composition containing zinc (e.g., zinc oxide) increases the substantivity of zinc on a skin surface as compared to a comparative composition without the film-forming polymer.

Compositions

The antiperspirant/deodorant compositions of the present disclosure are of stick form or in the form of cream, or flowable gel. In an aspect, the antiperspirant/deodorant composition includes base composition and an antiperspirant active and a film-forming polymer dispersed in the base composition, with the antiperspirant active being essentially a zinc-based antiperspirant active. The base composition includes a carrier that includes polyhydric alcohol or is a mixture of a polyhydric alcohol and water and a thickening agent that includes a $C_{14-22}$ fatty acid salt. In at least one implementation, the base composition includes the $C_{14-22}$ fatty acid salt. In another implementation, the base composition may be free or substantially free of the $C_{14-22}$ fatty acid salt.

The zinc-based antiperspirant active may include one or more of zinc oxide, zinc hydroxide, zinc hydroxide ions with counter ions, and zinc ions with counter ions, such as, for example, ZnO, $Zn^{2+}(aq)$, $Zn(OH)^+(aq)$, $Zn(OH)_2(aq)$, $Zn(OH)^-(aq)$, and $Zn(OH)^{2-}(aq)$. Non-limiting examples of counter ions include, halides, carboxylate based fatty acid salt, amino acid salt, cationic surfactants, zwitterionic surfactant, etc.

The antiperspirant effect of the antiperspirant/deodorant composition of the present disclosure is provided by the combination of a fatty acid salt, a zinc-based antiperspirant active, and optionally a film-forming polymer. In at least one implementation, the fatty acid salt may be provided by fatty acids already present on surfaces of the skin. In another implementation, the fatty acid salts may be provided by the antiperspirant/deodorant composition.

In one aspect, the antiperspirant effect of the antiperspirant/deodorant compositions of the present disclosure is provided by the combination of a fatty acid salt and a zinc-based antiperspirant active, which may be zinc oxide, zinc hydroxide, zinc hydroxide ions with counter ions, and zinc ions with counter ions and/or mixtures thereof, rather than by an aluminum-based antiperspirant active. The antiperspirant/deodorant compositions including the zinc-based antiperspirant active may also include at least one of aluminum-based antiperspirant actives, magnesium-based actives such as, for example, magnesium salts and magnesium hydroxide, and tin-based actives. In another aspect, any of the antiperspirant/deodorant compositions disclosed herein including a zinc-based antiperspirant active may be replaced or substituted for a magnesium-based active, an aluminum-based active, and/or a tin-based active.

In one aspect, the antiperspirant effect of the antiperspirant/deodorant compositions of the present disclosure is provided by the combination of a fatty acid salt and a zinc-based antiperspirant active, which may be zinc oxide, zinc hydroxide, zinc hydroxide ions with counter ions, and zinc ions with counter ions and/or mixtures thereof, rather than by an aluminum-based antiperspirant active. Thus, the compositions described in the present disclosure are essentially free of added aluminum-based antiperspirant actives and magnesium-based actives such as, for example, magnesium salts and magnesium hydroxide.

By the term "essentially free of added aluminum-based antiperspirant actives, and magnesium-based actives, it is meant that aluminum-based antiperspirant actives and magnesium-based actives are not added to the antiperspirant/deodorant composition in an amount that could display some antiperspirant/deodorant effect. However, aluminum-based antiperspirant actives and magnesium-based actives may be present in small or trace amounts due to contamination from other ingredients used in the making of the antiperspirant/deodorant formulations of the present disclosure.

As used herein, the term "aluminum-free" means that the composition does not contain any aluminum-based antiperspirant. Non-limiting examples of aluminum-based antiperspirant actives, include those listed in US antiperspirant monograph, such as, for example, aluminum chlorohydrate, aluminum chloride, aluminum sesquichlorohydrate, zirconyl hydroxychloride, aluminum-zirconium glycine complex (for example, aluminum zirconium trichlorohydrex gly, aluminum zirconium pentachlorohydrex gly, aluminum zirconium tetrachlorohydrex gly and aluminum zirconium octochlorohydrex gly), aluminum chlorohydrex PG, aluminum chlorohydrex PEG, aluminum dichlorohydrex PG, and aluminum dichlorohydrex PEG. In an embodiment, the antiperspirant/deodorant compositions of the present disclosure are aluminum-free antiperspirant/deodorant compositions.

Examples of magnesium-based actives include, but are not limited to, magnesium chloride, magnesium bromide, magnesium fluoride and organic salts such as various alkyl chain length substituted carboxylic acids, magnesium oxide, and magnesium hydroxide.

In an embodiment, "essentially free of a metal salt based antiperspirant active", it is meant that the antiperspirant/deodorant composition may contain less than 0.1 weight %, less than 0.05 weight %, or less than 0.01 weight %, of a metal based antiperspirant actives, as described below, or that the antiperspirant/deodorant composition contains no of metal salt based antiperspirant active.

The antiperspirant/deodorant composition of the present disclosure may include an antiperspirant active that is primarily a zinc-based antiperspirant active present in an amount of from 0.05 to 15 weight %, or 0.1 to 10 weight %, or 0.5 to 10 weight %, based on the total weight of the antiperspirant/deodorant composition. The zinc-based antiperspirant active in the form of zinc oxide can be incorporated into the antiperspirant/deodorant compositions by dispersing zinc oxide in the base composition. Zinc oxide present in the antiperspirant/deodorant composition may convert partially to zinc hydroxide or maybe present as zinc ions, or zinc hydroxide ions depending upon the pH of the final antiperspirant/deodorant composition. Hence, the amount of zinc oxide initially added to form the antiperspirant/deodorant compositions of the present disclosure may differ from the final amount of zinc oxide present in the composition due to conversion to zinc hydroxide and/or zinc ions depending upon the pH of the final antiperspirant/deodorant composition.

The pH of the antiperspirant/deodorant composition of the present disclosure can be in the range of 7 to 11, or 7 to 10.5, or 8 to 10, or 8.5 to 10, or 9 to 10.

Film-Forming Polymer

The antiperspirant/deodorant compositions of the present disclosure can also include a film-forming polymer. The film-forming polymer(s) present in the antiperspirant/deodorant compositions of the present disclosure may further enhance zinc substantivity on a skin surface. Any suitable film-forming polymer may be used in the antiperspirant/deodorant composition of the present disclosure, including but not limited to, one or more of a maleic anhydride copolymer such as polyvinyl methyl ether/maleic anhydride (PVM/MA decadiene crosspolymer), which is a copolymer of maleic anhydride and methyl vinyl ether crosslinked with 1,9-decadiene; a mixture of polyester-10 and propylene glycol dibenzoate; a mixture of polyester-7 and neopentyl glycol diheptanoate; adipic acid/diglycol crosspolymer;

trimethylpentanediol/adipic acid/glycerin crosspolymer (a copolymer of trimethylpentanediol and adipic acid crosslinked with glycerin); trimethylpentanediol/adipic acid copolymer; and capryloyl glycerin/sebacic acid copolymer.

In an embodiment, the film-forming polymer is a maleic anhydride copolymer, such as a copolymer of maleic anhydride and methyl vinyl ether crosslinked with 1,9-decadiene (PVM/MA decadiene crosspolymer). The film-forming polymer—PVM/MA decadiene crosspolymer—is commercially available as APShield™ 100, from the Ashland Specialty Ingredients Company of Bridgewater, N.J. Without wishing to be bound by theory, it is believed that the PVM/MA decadiene crosspolymer will interact with the zinc-based antiperspirant active in the formulation to create a hydrophobic film on the skin that enhances the water-resistant characteristics of the PVM/MA decadiene crosspolymer and increases the substantivity of zinc on a skin surface and also reduces apparent perspiration by preventing sweat from reaching the skin surface. The PVM/MA decadiene crosspolymer present in the antiperspirant/deodorant compositions of the present disclosure may also reduce the stinging potential when applied in the applied to the skin, such as an axillary area of a person.

The film-forming PVM/MA decadiene crosspolymer, for use as a zinc substantivity enhancer can be included in any desired amount. In one embodiment, the total amount of the film-forming polymer is in the range of 0.1 to 5 weight %, or 0.2 to 4 weight %, or 0.25 to 3 weight %, based on the total weight of the antiperspirant/deodorant composition.

Another suitable hydrophobic film-forming polymer is polyester-10, available as a mixture of polyester-10 and propylene glycol, known under the trade name of LexFilm® Spray, from the Inolex Chemical Company of Philadelphia, Pa. Without wishing to be bound by theory, it is believed that the polyester-10 present in the hydrophobic film-forming polymer composition will spread quickly on a skin surface with improved skin feel and limited interaction with the skin. In addition, the highly water-resistant characteristics of the polyester-10 should aid in both increasing substantivity of zinc on a skin surface and also in reducing apparent perspiration by preventing sweat from reaching the skin surface.

In an embodiment, the film-forming polymer composition may be a mixture of polyester-10 and propylene glycol dibenzoate. The mixture of polyester-10 and propylene glycol dibenzoate as a film-forming polymer composition, for use as a zinc substantivity enhancer can be included in any desired amount. In one embodiment, the total amount of the film-forming polymer mixture of polyester-10 and propylene glycol dibenzoate may be in the range of 0.1 to 4.5 weight %, or 0.5 to 4 weight %, or 1.0 to 3.6 weight %, based on the total weight of the antiperspirant/deodorant composition.

Other suitable examples of commercially available film-forming polymer composition include, but are not limited to a mixture of polyester-7 and neopentyl glycol diheptanoate as LexFilm® Sun; adipic acid/diglycol crosspolymer as Lexorez® 100; trimethylpentanediol/adipic acid/glycerin crosspolymer as Lexorez® 200; trimethylpentanediol/adipic acid copolymer as Lexorez® TL-8; trimethylpentanediol/adipic acid/Glycerin crosspolymer as WetFilm™; capryloyl glycerin/sebacic acid copolymer as Vellaplex™ all from the Inolex Chemical Company of Philadelphia, Pa.

In yet another embodiment, the film forming polymer is an acyl substituted polyvinylpyrrolidone having an average acyl chain length of 16 to 30 carbon atoms or 18 to 30 carbon atoms, or is an acyl substituted polyvinylpyrrolidone having an acyl chain length of 30 carbon atoms. The acyl substituted polyvinylpyrrolidone is present in an amount of 0 to 6 weight %, or 0.05 to 6 weight %, based on the total weight of the antiperspirant/deodorant composition.

Non-limiting examples of commercially available acyl substituted polyvinylpyrrolidone (PVP) include Triacontanyl PVP having an acyl chain length of 30 carbon atoms as Unimer U-6; VP/Eicosene Copolymer having an acyl chain length of 20 carbon atoms as Unimer U-15; VP/Hexadecene Copolymer having an acyl chain length of 16 carbon atoms as Unimer U-151; VP/Hexadecene Copolymer, Octyldodecanol, having a mixture of two different alkyl chain lengths with an estimated average acyl chain length of 19 carbon atoms as Unimer U-1946, all available from Induchem USA Inc. of New York, N.Y. Additionally, a Triacontanyl PVP can also be obtained from Ashland Specialty Ingredients with the trade name Ganex™ WP-660 and as Vida-Care AVP-30 from Lambson Ltd of West Yorkshire UK; VP/Eicosene Copolymer as Vida-Care AVP-20; and VP/Hexadecene Copolymer Vida-Care AVP-16 from Lambson Ltd of West Yorkshire UK.

Carrier

The carrier present in the antiperspirant/deodorant compositions of the present disclosure primarily includes a polyhydric alcohol or is a mixture of a polyhydric alcohol and water. In one embodiment, the polyhydric alcohol present in the antiperspirant/deodorant compositions of the present disclosure includes one or more organic compounds which contain about 2 to about 6 carbon atoms and about 2 to about 6 hydroxy groups. Suitable polyhydric alcohols include, but are not limited to, ethylene glycol, propylene glycol, 1,3-propanediol, trimethylene glycol, butylene glycol, diethylene glycol, dipropylene glycol, glycerin, sorbitol, xylitol and mixtures thereof. In one embodiment, the polyhydric alcohol is propylene glycol or dipropylene glycol or a mixture thereof. In an embodiment, the polyhydric alcohol includes or is propylene glycol. The polyhydric alcohol can be present in any suitable amount in the antiperspirant/deodorant compositions of the present disclosure. For example, the polyhydric alcohol may be present in an amount of from about 50 weight %, about 55 weight %, about 60 weight %, about 65 weight %, about 70 weight %, or about 75 weight % to about 80 weight %, about 85 weight %, about 90 weight %, about 95 weight %, or about 95 weight %. In an exemplary implementation, the polyhydric alcohol may be present in an amount of from about 50 weight % to about 85 weight % or about 98 weight %, or from about 72 weight % to 93 weight %, based on the total weight of the antiperspirant/deodorant composition.

In an embodiment, water may be added in the amount of 0.1 to 20 weight %, based on the total weight of the composition.

In an embodiment, the antiperspirant/deodorant composition is essentially free of morpholine, pyridine, acetic acid, ethylene carbonate, propylene carbonate, N-methyl pyrrolidone, pyrrolidone, butyrolactone, dimethylsulfoxide, dimethyl formamide, 2-ethoxyethanol, caprolactam and the like.

Thickening Agent

The antiperspirant/deodorant compositions of the present disclosure may include a saturated and/or unsaturated $C_{14-22}$ fatty acid salt, which may be an alkali metal, an alkaline earth metal, transition metal, or an amine salts of $C_{14-22}$ fatty acid. Suitable examples of $C_{14-22}$ fatty acid include, but are not limited to myristic, palmitic, stearic, arachidic, behenic, oleic, linoleic, linolenic acid and mixtures thereof. In another embodiment, the $C_{14-22}$ fatty acid salt comprises one or more counterions chosen from sodium, potassium, calcium, magnesium, zinc, diethylamine, triethyl amine and mixtures thereof. In one embodiment, the fatty acid salt is a $C_{16-22}$ fatty acid salt. In another embodiment, the fatty acid salt is a $C_{18-22}$ fatty acid salt. In another embodiment, the $C_{16-22}$ fatty acid salt is chosen from sodium stearate, potassium stearate, aluminum monostearate, sodium oleate, sodium palmitate, sodium behenate, diethylamine stearate, triethylamine stearate, triethylemine oleate, and mixtures thereof. In one embodiment, the $C_{14-22}$ fatty acid salt is present in an amount of 0 to 8 weight %, or 3 to 7 weight %, or 5 to 7 weight %, based on the total weight of the antiperspirant/deodorant composition.

One purpose of the $C_{14-22}$ fatty acid salts is to thicken the antiperspirant/deodorant composition so that it functions as a "stick-type" deodorant. As such, the $C_{14-22}$ fatty acid salts may be referred to herein as a thickening agent, a gelling agent or a structurant. It should be appreciated that the fatty acid may be pure fatty acid or a commercial product including the primary fatty acid in combination with or mixed with other minor fatty acids.

In one embodiment, the antiperspirant/deodorant compositions of the present disclosure may include an ester of glycerin and a $C_{10-18}$ fatty acid. The $C_{10-18}$ fatty acid may be chosen from caprylic, capric, lauric, myristic, palmitic, stearic, oleic, linoleic, and linolenic acids and mixtures thereof. In one embodiment, the $C_{10-18}$ fatty acid ester is present in the compositions of the present disclosure in an amount of 0 to 0.8 weight %, or 0.2 to 0.7 weight %, or 0.3 to 0.6 weight %, based on the total weight of the antiperspirant/deodorant composition.

Optional Ingredients

The antiperspirant/deodorant compositions of the present disclosure may also include other ingredients. For example, the antiperspirant/deodorant compositions of the present disclosure may include one or more ingredients for achieving and maintaining a desired consistency, one or more ingredients for giving the product a soothing skin feel, one or more antioxidants, one or more fragrances and one or more ingredients for fragrance duration or retention, additional deodorizing agent, and clarifier-surfactant. Some ingredients listed herein can provide more than one function to the compositions. For example, certain emollients can act as lipophilic carrier material and a gelling agent at the same time.

Non-limiting examples of ingredients suitable for use in achieving and maintaining desired consistency are, for example, caprylic capric triglyceride, capryl glycol, glycerin, and glyceryl laurate.

Non-limiting examples of ingredients suitable for use as skin soothing agents are, for example, aloe vera leaf extract or juice, chamomile aqueous extract, other herbal extracts and oatmeal. Non-limiting examples astringents include, for example witch hazel water. The present antiperspirant/deodorant compositions may include one or more of aloe vera leaf extract or juice present in an amount of 0.5 to 10 weight %, witch hazel (also known as witch hazel water) present in an amount of 1 to 10 weight %, and chamomile aqueous extract present in an amount of 1 to 20 weight %, based on the total weight of the antiperspirant/deodorant composition.

Non-limiting examples of ingredients suitable for use as antioxidants are, for example, one or more of tocopherol and its derivatives, butyl hydroxyanisole (BHA), butyl hydroxytoluene (BHT), erythorbic acid, propyl gallate, sodium erythorbate, tertiary butyl hydroquinone (TBHQ), rosemary extract and, more preferably, ascorbic acid and salts thereof. The antioxidant compound may be one or more of tocopherol and its derivatives present in an amount of 0.001 to 0.5 weight %, or butyl hydroxyanisole (BHA) present in an amount of 0.0075 to 0.1 weight %, butyl hydroxytoluene (BHT) present in an amount of 0.005 to 0.02 weight %, erythorbic acid present in an amount of 0.05 to 1 weight %, propyl gallate present in an amount of 0.01 to 1 weight %, sodium erythorbate present in an amount of 0.05 to 1 weight %, tertiary butyl hydroquinone (TBHQ) present in an amount of 0.005 to 0.1 weight %, rosemary extract present in an amount of 0.02 to 0.4 weight %, and ascorbic acid and salts thereof present in an amount of 0.01 to 0.1 weight %, based on the total weight of the antiperspirant/deodorant composition.

The antiperspirant/deodorant compositions of the present disclosure may include natural and synthetic fragrance(s), if a scented product is desired. Fragrances can be used in any suitable amount, such as in the range of 0.01 to 3%, and, for example, at a level of about 1%.

The antiperspirant/deodorant compositions of the present disclosure may also include ingredients suitable for use for fragrance duration or longevity, such as, for example silica shells, polymeric, or other encapsulates compatible with antiperspirant/deodorant base formulation.

The antiperspirant/deodorant compositions of the present disclosure may include additional deodorizing compounds, antimicrobials, and/or preservatives, for example, including but not limited to, capryl glycol, glyceryl laurate, capric triglyceride, benzoic acid, sodium benzoate, hydroxybenzoate and derivatives, lactic acid, phenoxyethanol, ethoxy hexyl glycerine, benzyl alcohol, Kathon™ and Kathon™ CG, present in an amount of 0.1 to 4 weight %, and lemongrass oil present in an amount of 0.01 to 0.1 weight %, based on the total weight of the antiperspirant/deodorant composition.

The antiperspirant/deodorant compositions of the present disclosure may include a clarifier-surfactant, including, but not limited to, pentadoxynol-200, tetra(hydroxypropyl)diamine, 2-amino-2-methylpropanol, 2-amino-2-hydroxymethyl-1,3-propanediol, poly($C_{2-4}$ alkylene) glycol ethers of $C_{12-22}$ fatty alcohols in which the polyalkylene glycol portion contains from about 10 to about 100 alkyleneoxide repeating units. In an embodiment, the clarifier-surfactant may include from among laureth-10, laureth-20, laureth-30. laureth-40, PEG-10 Myristyl Ether, steareth-10, steareth-20, steareth-40, steareth-100, PEG-50 Stearyl Ether, steareth-100, beheneth-20 and mixtures thereof. In another embodiment, the clarifier-surfactant includes or is polyoxyethylene 3-pentadecyl phenyl ether. The clarifier-surfactant may be present in the antiperspirant/deodorant compositions of the present disclosure in an amount of 2 to 3.5 weight %, based on the total weight of the antiperspirant/deodorant composition.

Additional gelling agent(s) such as, fatty alcohols may be incorporated into the antiperspirant/deodorant compositions of the present disclosure. In one embodiment, the fatty alcohol is stearyl alcohol or docosyl alcohol (behenyl alcohol).

In one embodiment, the antiperspirant/deodorant compositions of the present disclosure have an appearance consistent with the product appearing clear, essentially clear, or non-visible when applied to the user's body. In this regard, the antiperspirant/deodorant compositions of the present disclosure may appear opaque, turbid, or colored when formed into a shape consistent with a final antiperspirant/deodorant product (e.g., shapes know in the art as used for stick-type deodorants) as long as the product is clear, essentially clear, or non-visible when applied to the user's body in amounts consistent with typical use. A definition of clear is that it is not highly visible after application and equilibration in the underarm.

The antiperspirant/deodorant compositions according to the present disclosure can be packaged in conventional containers, using conventional techniques. For example, where the composition is a stick composition, the composition, while still in liquid form, can be introduced into a dispensing package as conventionally done in the art, and cooled therein so as to thicken in the package. Thereafter, the product can be dispensed from the dispensing package as conventionally done in the art, to deposit the active material, for example, on the skin. This provides good deposition of the active material on the skin. Other methods of producing a final antiperspirant/deodorant product may include those taught in U.S. Pat. No. 7,128,901 to Jonas, et al., wherein the product is formed into a stick-like shape without the heating/melting step typical of these processes, or reasonable variations thereof. The antiperspirant/deodorant compositions according to the present disclosure may be in the form of cream, or flowable gel instead of stick form and may be dispensed through appropriate packaging such as roll-ons, tubes, or gels containers.

The antiperspirant/deodorant compositions of the present disclosure may be applied to the skin, such as an axillary area of a person using conventional techniques suitable for stick, cream, or flowable gel, and in a manner that would result in typical loading as used for underarm products. For example, for use as an antiperspirant/deodorant composition, the loading can be in an amount of about 0.5 to 10 mg/cm$^2$, or about 2 to about 9 mg/cm$^2$, or about 5 mg/cm$^2$.

Zinc Substantivity

The antiperspirant/deodorant composition provides excess zinc substantivity on skin [e.g., from zinc oxide, or zinc hydroxide, zinc hydroxide, or zinc ions] in an amount of at least 8 picoMoles or at least 50 picoMoles per 0.34 cm$^2$ of skin surface, as measured by the method disclosed hereinbelow.

As used herein, the zinc substantivity is measured by applying a sample of the antiperspirant/deodorant composition onto a sample of pig skin and equilibrating in a hydrated form for 15 hours at approximately 5° C., followed by rinsing the pig skin five times with 100 μl of 0.1 M NaCl solution to simulate perspiration or sweating. A color-changing zinc-sensitive dye solution was then applied to the pig skin and the amount of zinc was determined from the color change. The method of measuring zinc substantivity is described in details below under Example section.

Without wishing to be bound by theory, it is believed that the testing for zinc substantivity done on pig skin using 100 μL NaCl solution to simulate sweating on human skin is representative of zinc sub stantivity provided by the antiperspirant/deodorant composition of the present disclosure on human skin.

Methods/Uses

In an aspect, there is a method of reducing apparent perspiration including applying the antiperspirant/deodorant composition, as disclosed hereinabove to an axillary area of a person, wherein the antiperspirant/deodorant composition reduces apparent perspiration, wherein the reduction is in comparison to an antiperspirant/deodorant composition without the combination of zinc oxide, a fatty acid salt, and a film-forming polymer.

In yet another aspect, a film-forming polymer in combination with a fatty acid salt and zinc-based antiperspirant active can be used in the antiperspirant/deodorant composition as disclosed hereinabove for at least one of the following, when applied to an axillary area of a person:
   a) increase sub stantivity of zinc on a skin surface,
   b) enhance resistance to hydrostatic pressure present in the sweat ducts, and
   c) reduce visible residue,
wherein the film-forming polymer comprises at least one of a copolymer of maleic anhydride and methyl vinyl ether crosslinked with 1,9-decadiene; a mixture of polyester-7 and neopentyl glycol diheptanoate; adipic acid/diglycol crosspolymer; trimethylpentanediol/adipic acid/glycerin crosspolymer; and trimethylpentanediol/adipic acid copolymer; capryloyl glycerin/sebacic acid copolymer, and an acyl substituted polyvinylpyrrolidone having an average acyl chain length of 16 to 30 carbon atoms.

The antiperspirant/deodorant composition of the present disclosure provides an increase in resistance to hydrostatic pressure as measured via the filter treatment method outlined below, and which may be present in the sweat ducts, in an amount of 20% or at least 30% or at least 40%, as compared to resistance to hydrostatic pressure provided by a comparative antiperspirant/deodorant composition having an identical composition as that of the antiperspirant/deodorant composition of the present disclosure, except that the comparative antiperspirant/deodorant composition has a film-forming polymer of the present disclosure in combination with either zinc oxide or a fatty acid salt. In an embodiment, the film forming polymer is a copolymer of maleic anhydride and methyl vinyl ether crosslinked with 1,9-decadiene. In an embodiment, the fatty acid salt is derived from stearic acid.

The antiperspirant/deodorant composition of the present disclosure provides a reduction in visible residue on skin upon application of the antiperspirant/deodorant on a surface of the skin, in an amount of at least 10%, or at least 30%, or at least 50%, as measured by the method disclosed hereinbelow, as compared to the visible residue provided by a comparative antiperspirant/deodorant composition having an identical composition as that of the antiperspirant/deodorant composition of the present disclosure, except that the comparative antiperspirant/deodorant composition has no film-forming polymer of the present disclosure. In an embodiment, the film forming polymer is a PVM/MA decadiene crosspolymer—a copolymer of maleic anhydride and methyl vinyl ether crosslinked with 1,9-decadiene.

Figure 4A:
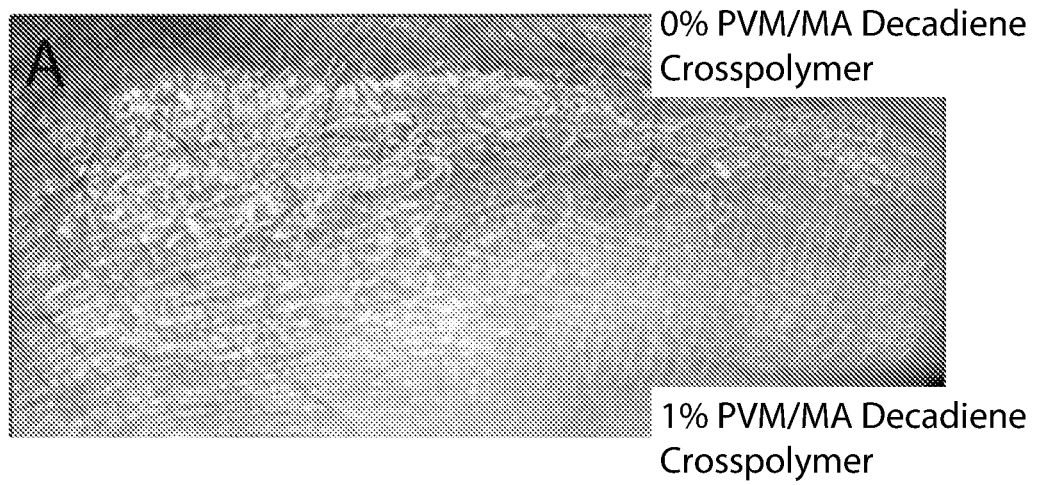
FIG. 4A shows a photograph of white residue level after application by 10 rubs for 10 seconds of 50 mg of antiperspirant/deodorant composition of the present disclosure comprising 10 weight % zinc oxide and with or without 1 weight % of PVM/MA decadiene crosspolymer.
Figure 4B:
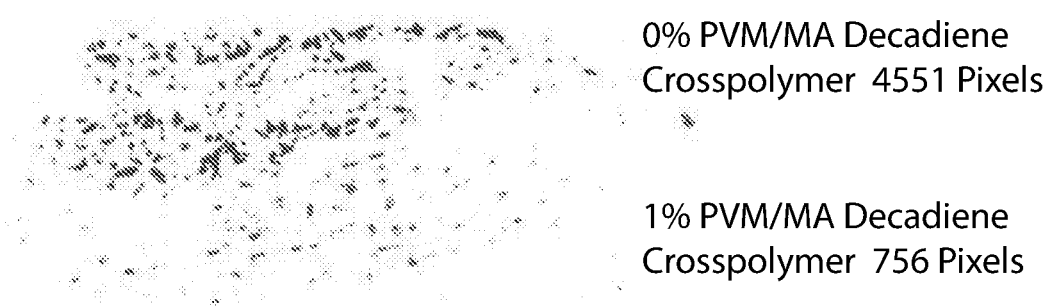
FIG. 4B shows a histogram segmentation analysis, based on visual analysis, of the optical images of the sample shown in FIG. 4A to quantify the white residue.

FIG. 4A shows a photograph of white residue level after application by 10 rubs for 10 seconds of 50 mg of antiperspirant/deodorant composition of the present disclosure comprising 10 weight % zinc oxide and with or without 1 weight % of PVM/MA decadiene crosspolymer. FIG. 4B shows an optical image, of the sample shown in FIG. 4A. Histogram segmentation to identify white residue of the images shown in FIG. 4B showed approximately 6 fold reduction in white residue with the addition of 1 weight % of PVM/MA decadiene crosspolymer.

In yet another aspect, a zinc substantivity enhancer can be used in the antiperspirant/deodorant composition as disclosed hereinabove to increase zinc retention when applied to an axillary area, such as an armpit, wherein the substantivity enhancer is a film-forming polymer composition comprising PVM/MA decadiene crosspolymer.

In an aspect, there is an antiperspirant/deodorant composition including:
   a) a base composition that includes:
     (i) a carrier which is primarily a polyhydric alcohol or a mixture of a polyhydric alcohol and water, wherein the polyhydric alcohol comprises an organic compound containing 2 to 6 carbon atoms and 2 to 6 hydroxy groups;

(ii) a thickening agent that includes a $C_{14-22}$ fatty acid salt, wherein the $C_{14-22}$ fatty acid salt includes at least one of an alkali metal, an alkaline earth metal, a transition metal, or an amine salt of $C_{14-22}$ fatty acid;

b) an antiperspirant active dispersed in the base composition, wherein the antiperspirant active is a zinc-based antiperspirant active, and wherein the antiperspirant/deodorant composition is essentially free of aluminum-based antiperspirant actives and magnesium-based actives;

The antiperspirant/deodorant compositions of the present disclosure provide several advantages over conventional antiperspirant/deodorant compositions. First and foremost is that the antiperspirant/deodorant compositions are free or substantially/essentially free of aluminum, as aluminum has been perceived to have adverse side effects in some people. Secondly, the antiperspirant/deodorant compositions as disclosed hereinabove provides increased resistance to hydrostatic pressure that may be present in the sweat ducts. Furthermore, the presence of film-forming polymer has been found to improve rheological properties of the antiperspirant/deodorant composition by reducing gel hardness. Furthermore, the film forming polymers in combination with zinc oxide and fatty acid salt in the antiperspirant/deodorant compositions of the present disclosure provide improved homogeneous deposition of zinc oxide, there resulting in reduced visible residue of zinc oxide on the skin.

EXAMPLES

Test Method

Method of Measuring Zinc Substantivity

The zinc substantivity was measured by applying a sample of the antiperspirant/deodorant composition to be tested onto the outer side, referred to as the stratum corneum, of a sample of pig skin resulting in 5.88 µl/cm² of the antiperspirant composition on the pig skin and equilibrating in a hydrated form for 15 hours at approximately 5° C. The pig skin sample was in a plug shape, approximately 0.66 cm in diameter, and placed in a standard 96 well cultured plate for the experiments. The pig skin sample was then rinsed five times with 100 µl of 0.1 M NaCl solution to simulate perspiration or sweating. A color-changing zinc-sensitive dye solution [4-(2-Pyridylazo)resorcinol] was then applied to the sample after rinsing with 0.1 M NaCl and then the color change was measured using photographic techniques. The color-changing zinc-sensitive dye solution was applied in an amount needed to ensure adequate and detectable color change in the potential zinc concentration ranges left on the skin surface. Images were captured at two minute intervals for up to seven hours and the concentration of the zinc was measured by following the development of a red color in the solution with time and correlating against standard curves. The standard curves were generated by combining known amounts of zinc ion and dye and measuring appropriate color change at each time point within the experiment. The amount of desorbed zinc was determined using the colorimetric photography method and analyzed using a multivariant ANOVA for a subset of the time determined by the maximum amount of zinc that can be detected by the dye in solution using the standard curve.

Efficacy Test using Starch/Iodine Test

A forearm starch/iodine test may be used as a rapid screening tool for underarm formulations prior to underarm clinical testing. The following procedure may be used for all tests discussed in this patent document. The panelists should be chosen who had not placed any antiperspirant products on their interior forearms for at least 14 days prior to the start of the test. Test formulations are applied on the inner forearms in preselected amounts. A control product such as a high efficacy aluminum, zirconium-based antiperspirant stick is applied to one site on the panelists' arms as a positive control. After application of the formulations, the sites are occluded with covering chambers for one hour under conditions of about 40° C. and 30% relative humidity. Panelists then remove the covering chambers. One hour after removal of the covering chambers, the forearms are each washed with a mild soap. This is repeated for the first two days of the study. On the third day of product application, the sites are occluded for one (1) hour, but are not washed with soap. The panelists perform their normal cleansing regimen using a mild soap during the course of the study. Approximately 20 hours after the last application of the products, the panelists are equilibrated in a room at 40° C. (105° F.) and 40% relative humidity for 15 minutes. In another version of this test, the panelists exercised on a stationary bike for 20 minutes instead of being equilibrated in a room at 40° C. (105° F.) and 40% relative humidity for 15 minutes, prior to the application of test paper strips. The panelists arms are then patted dry with a paper towel followed by application of paper strips impregnated with iodine to the test sites. Exposure to sweat causes the paper to turn purple at sites of hydration, generating a spatial map of the firing sweat glands. The papers are removed once the purple spots begin to appear on the backside or after five minutes, whichever comes first. Images of the papers may be digitized to quantify the amount of purple spot coverage. Once images are digitized, the area for measurement is identified using the same area as occluded by the chambers. A comparison of the total area of hydration for treated skin versus untreated sites is used to calculate a % Sweat Reduction (Eq:1). The area of sweat from untreated sites used in Equation 1 is calculated as the mean sweat areas of all the untreated sites directly adjacent to the treated site of interest. Since the number of firing sweat glands varies along the surface of the volar forearm, the mean sweat area of the adjacent untreated sites is used to approximate the area of sweat which would have been produced if a formula had not been applied to the treatment site.

$$\% \text{ Sweat Reduction} = 100 \times \left[1 - \frac{\text{area treated}}{\text{mean area untreated}}\right] \quad (1)$$

Resistance to Hydrostatic Pressure:

Resistance of films of antiperspirant/deodorant composition of the present disclosure to hydrostatic pressure due to that would be experienced at the outlet of a sweat duct was determined in a simulated environment using a filter treated with the antiperspirant/deodorant composition and measuring the permeation coefficient of the coated filter for 0.1 molar sodium chloride. The permeation coefficient (κ) can be determined using Darcy's law, which provides a relationship between the instantaneous discharge rate (Q) through a porous medium, the viscosity of the fluid (η) and the pressure drop (ΔP) over a given distance (L):

$$\kappa_i = (Q_i \cdot \eta \cdot L)/(A \cdot \Delta P_i) \quad (1)$$

Where:
   κ=Permeation Coefficient for Volume i (units, e.g., μD or darcy unit))
   $Q_i$=Flow Rate for Volume i (units of volume per time, e.g., m³/s)
   η=Fluid Viscosity ((units of viscosity, e.g., Pa·s)
   L=Filter+Sample Thickness (units of length, e.g., m)
   A=Cross Sectional Area of Flow (units of area, e.g., m²)
   $\Delta P_i$=Pressure Drop Across Filter for Volume i (units of pressure, e.g., pascals)

The darcy unit is referenced to a mixture of unit systems. A porous medium with a permeability of 1 darcy permits a flow of 1 cm³/s of a fluid with viscosity 1 cP (1 mPa·s) under a pressure gradient of 1 atm/cm acting across an area of 1 cm². A millidarcy (md) is equal to 0.001 darcy and a microdarcy (0) equals 0.000001 darcy.

Essentially a known amount of antiperspirant/deodorant composition of the present disclosure was spread evenly onto a cellulosic filter with a 20 μm equivalent pore size. The filters with treated side up were equilibrated for approximately 15 hours over filters saturated with 100 mM NaCl. The formula treated filters are then removed, allowed to air dry, then filtered treated side down (negative pressure) or to simulate the hydrostatic conditions observed in, and at the surface, of sweat ducts. The permeation coefficient was then measured as a function of one or more of chain length of fatty acid, amount of ZnO, amount of PVM/MA decadiene crosspolymer.

As can be seen from equation (1), a reduction in the permeation coefficient reflects enhanced resistance to hydrostatic pressure. Increased resistance to hydrostatic pressure is expected to be consistent with an increase in antiperspirant benefits due to plug formation or superficial blockage in the sweat ducts. In addition, by comparing the permeation coefficients with positive and negative pressure, one can estimate the relative "stickiness" of the formula aggregates compared to simple physical blocking of the pores. In other words, maintaining a small permeation coefficient with negative pressure indicates not only resistance to hydrostatic pressure, but also enhance adhesion of the formula aggregates to each other. Without wishing to be bound by theory, it is believed that an increase in aggregate adhesion would lead to enhanced benefits. Increased resistance to hydrostatic pressure is also expected to reflect an increase in antiperspirant benefits due to plug formation and pore blockage in the sweat ducts.

Example 1

Aluminum-Free Antiperspirant/Deodorant Composition Comprising Zinc Oxide

Various antiperspirant/deodorant compositions shown in Table 1 were prepared as follows: Weighed propylene glycol into a beaker and heated to 75° C. while mixing using a high shear mixing blade. While maintaining the temperature at 75° C., added stearic acid to the propylene glycol with continuous mixing at 500 rpm until completely dissolved, followed by dropwise addition of caustic (50% NaOH) while maintaining the temperature constant and continuous mixing at 500 rpm until completely dissolved to form a base composition for an antiperspirant/deodorant composition in stick form. After compete dissolution of caustic, zinc oxide particles were dispersed in propylene glycol to form a uniform paste and then this paste was slowly added to the base composition while maintaining the temperature at 75° C. with continuous stirring, until the zinc oxide particles were completely dispersed. Added water, if used, while maintaining the temperature of the formulation at 75° C. with continuous mixing at 1000 rpm. Once water is completely dissolved, turned off the heat to allow the antiperspirant/deodorant formulation to cool off to approximately 60° C., while adjusting the mixing speed as necessary. Transferred the antiperspirant/deodorant formulation into a labeled sample collection jar and periodically shaking the jar for approximately 15-30 seconds to insure uniformity within the sample and to prevent precipitation of zinc oxide particles, as the cooling process continued and until the sample solidified.

TABLE 1

| Antiperspirant/Deodorant Composition: | | |
|---|---|---|
| Aluminum-free Antiperspirant/ deodorant composition | Example (Amounts in weight %) | |
|  | 1.1 | 1.2 |
| ZINC OXIDE | 10.0000 | 10.0000 |
| PROPYLENE GLYCOL USP, EP | 63.8800 | 63.2900 |
| DEMINERALIZED WATER | 17.6772 | 18.1262 |
| STEARIC ACID - TRIPLE PRESSED GRADE | 3.8176 | 4.1000 |
| C12-C22 LONG CHAIN STEARIC ACID | 2.2432 | 2.4000 |
| MEMBRANE CELL CAUSTIC - 50% NaOH | 1.6856 | 1.8078 |
| SODIUM CHLORIDE | 0.5025 | 0.0660 |
| STEARYL ALCOHOL | 0.1867 | 0.2000 |
| TETRASODIUM EDTA - 39% SOLN. | 0.0072 | 0.0100 |

The antiperspirant/deodorant formulations of Example 1.1 and 1.2 were tested for antiperspirant efficacy using standard gravimetric tests, the results of which are summarized below in Table 2.

TABLE 2

| Antiperspirant efficacy | | |
|---|---|---|
| Study Design | % Sweat Reduction a compared to Untreated | Formulation of |
| Underarm | 29 | Example 1.1 |
| Back | 33 | Example 1.1 |
| Back | 38 | Example 1.1 |
| Back | 23 | Example 1.2 |
| mean | 30.8 | |
| +/−SD | 6.3 | |
| n | 4 | |
| +95% | 41 | |
| −95% | 21 | |

As shown in the Table 2, addition of 10 weight % zinc oxide to a sodium stearate based antiperspirant/deodorant stick delivered a mean sweat reduction of 31% versus an untreated control site with a 95% confidence range of 21 to 41% sweat reduction in a meta-analysis of four independent tests.

Example 2

Effect of the Amount of Zinc Oxide on the Antiperspirant Efficacy

Table 3 summarizes the compositions of various antiperspirant/deodorant compositions prepared using the procedure of Example 1 with ZnO varying from 0 to 13 weight %, based on the total amount of the antiperspirant/deodorant composition.

TABLE 3

Dose response analysis of antiperspirant efficacy in stearate/propylene glycol bases

| Aluminum-free Antiperspirant/ | Example (Amount in weight %) | | | | Comparative |
|---|---|---|---|---|---|
| deodorant composition | 2.1 | 2.2 | 2.3 | 2.4 | Example A |
| ZINC OXIDE | 10.0000 | 13.0000 | 5.0000 | 2.0000 | 0.0000 |
| PROPYLENE GLYCOL USP, EP | 63.8800 | 61.7507 | 67.4289 | 69.5582 | 70.9778 |
| DEMINERALIZED WATER | 17.6772 | 17.0879 | 18.6592 | 19.2485 | 19.6413 |
| STEARIC ACID - TRIPLE PRESSED GRADE | 3.8176 | 3.6903 | 4.0297 | 4.1569 | 4.2417 |
| C12-C22 LONG CHAIN STEARIC ACID | 2.2432 | 2.1685 | 2.3679 | 2.4426 | 2.4925 |
| MEMBRANE CELL CAUSTIC - 50% NaOH | 1.6856 | 1.6295 | 1.7793 | 1.8355 | 1.8729 |
| SODIUM CHLORIDE | 0.5025 | 0.4858 | 0.5304 | 0.5472 | 0.5584 |
| STEARYL ALCOHOL C18 | 0.1867 | 0.1805 | 0.1970 | 0.2033 | 0.2074 |
| TETRASODIUM EDTA - 39% SOLN. | 0.0072 | 0.0069 | 0.0076 | 0.0078 | 0.0080 |
| % Sweat Reduction | 38.4 | 28.6 | 36.2 | 31.6 | 25.9 |
| $p < 0.05$ versus 0% ZnO | * | | * | | |

Table 3 shows that addition of 2-13 weight % of ZnO (Example 2.1-2.4) results in an improvement in % sweat reduction as compared to the antiperspirant composition with no zinc oxide (Comparative Example A). Further, statistical analysis of % sweat reduction showed that formulations with 5-10 weight % ZnO (Example 2.1 and 2.3) were statistically different from that with no ZnO ($p<0.05$) (Comparative Example A). This suggests that maximum efficacy is achieved between approximately 5 and 10 weight % of ZnO. Furthermore, a cubic polynomial fit to the % sweat reduction suggests that maximum antiperspirant efficacy would be achieved with about 8 weight % ZnO in the current sodium stearate gel base.

Antiperspirant Efficacy of ZnO as a Function of Time

Antiperspirant efficacy of antiperspirant/deodorant formulation containing 10 weight % of ZnO (Example 2.1) was measured in an underarm study compared to untreated area and the results after 1 hour and 24 hour are summarized in Table 4. The 24 hour measurement was performed on the same axilla after the initial 1 hour sweat test without further application of test product.

TABLE 4

Antiperspirant efficacy of 10 weight % ZnO at 1 hour and 24 hour

| | % Sweat Reduction (SR) vs. Untreated | |
|---|---|---|
| | 1 hr. | 24 hr. |
| Example 2.1 | 28.6 | 0.6 |
| | $p < 0.05$ (20% SR) | $p < 0.91$ (20% SR) |

The % sweat reduction measured at 1 hour meets the statistical criteria for a composition to show at least 20% reduction in perspiration to be effective as an antiperspirant. Interestingly, the antiperspirant effect disappeared after 24 hours when the sweat test was performed on the same axilla without application of additional product, and was found to be equivalent to the baseline untreated sites. This clearly shows that the antiperspirant/deodorant compositions containing ZnO as an antiperspirant active provide short term antiperspirant benefits without impacting the skin and with no long term changes in the skin's natural physiologic state. This absence of any long-term changes in the skin's natural physiologic state was further investigated by using starch/iodine test.

Figure 1B:
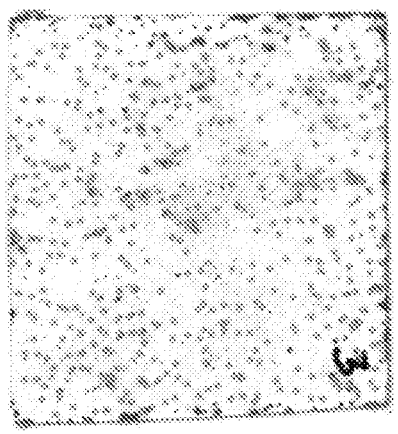
FIG. 1B is the same image as FIG. 1A, but with an overlay of firing sweat glands, which are common to both before and after treatment with an antiperspirant/deodorant composition of the present disclosure comprising 10 weight % zinc oxide.
Figure 1B:
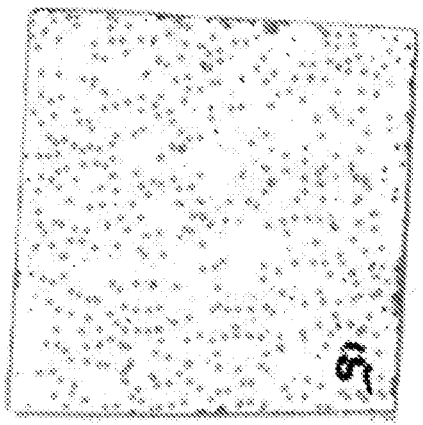
Figure 2A:
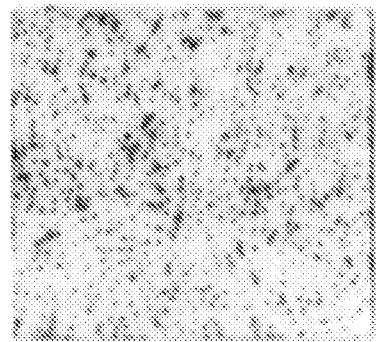
FIG. 2A shows an optical image of sweat producing glands of an untreated occluded site.
Figure 2B:
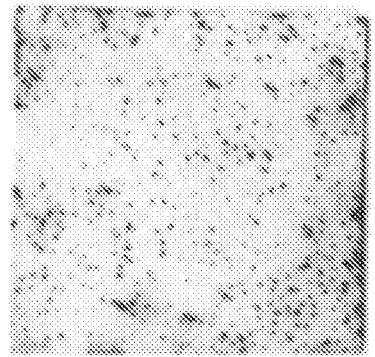
FIG. 2B shows an optical image of sweat producing glands of an occluded site, as shown in FIG. 2A, treated with a comparative aluminum-based antiperspirant/deodorant composition with no zinc oxide.
Figure 2C:
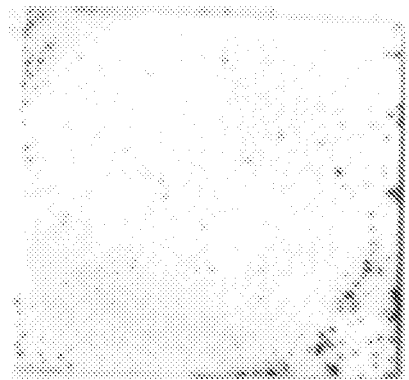
FIG. 2C shows an optical image of sweat producing glands of an occluded site, as shown in FIG. 2A, where the comparative aluminum-based antiperspirant/deodorant composition with no zinc oxide was applied after an additional perspiration cycle.

FIGS. 1A and 1B further provide evidence that 10 weight % ZnO does not cause significant long term blockage of sweat ducts when delivered from a gelled sodium stearate base on the forearm, as compared to standard aluminum and aluminum zirconium salts defined by the US antiperspirant monograph. FIG. 1A shows optical images of sweat glands producing perspiration identified by dark spots before and after treatment with an antiperspirant/deodorant composition of the present disclosure comprising 10 weight % zinc oxide respectively. FIG. 1B shows the same before and after images as shown in FIG. 1A, but with an overlay of firing sweat glands, which are common to both before and after treatment with an antiperspirant/deodorant composition of the present disclosure comprising 10 weight % zinc oxide. As can be seen from comparing FIG. 1A with 1B, that treatment with 10 weight % ZnO suspended in a gelled sodium stearate does not function similar to a traditional plug for a sweat duct. Instead, the treatment with 10 weight % ZnO suspended in a gelled sodium stearate allows for sweat to reach just below the surface in a region accessible by the fibers of the filter paper placed on the skin. Accordingly, the results indicate a different mechanism of action for the present composition. Furthermore, using pattern recognition methods, it can be shown that substantially same sweat glands are producing perspiration before and after treatment with the zinc oxide containing product. This is in direct contrast to a standard commercial antiperspirant where significant reduction in the number of firing sweat glands is detected after application of the product, as shown in FIGS. 2A-2C. FIG. 2A shows an optical image of sweat producing glands of an untreated occluded site. FIG. 2B shows an optical image of sweat producing glands of an occluded site, as shown in FIG. 2A, treated with a comparative aluminum-based antiperspirant/deodorant composition with no zinc oxide. FIG. 2C shows an optical image of sweat producing glands of an occluded site, as shown in FIG. 2A, where the comparative aluminum-based antiperspirant/deodorant composition with no zinc oxide was applied after an additional perspiration cycle.

Example 3

Antiperspirant/Deodorant Film Properties

Table 5 shows antiperspirant/deodorant composition comprising various amounts of zinc oxide and various $C_{14-22}$ fatty acid salts in propylene glycol as a carrier to deliver a sweat repellant film to the skin's surface:

TABLE 5

Premixing of ZnO in propylene

| | | | Phase 1 | | | | Phase 2 |
|---|---|---|---|---|---|---|---|
| Sample | Fatty Acid | Carbon Number | % Fatty Acid | % NaOH (50% in $H_2O$) | % Propylene Glycol | % ZnO | % Propylene Glycol |
| Control B | Myristic | 14 | 5.41 | 1.87 | 71.39 | 0.00 | 21.33 |
| Example 3.1 | Myristic | 14 | 5.41 | 1.87 | 71.39 | 2.00 | 19.33 |
| Example 3.2 | Myristic | 14 | 5.41 | 1.87 | 71.39 | 5.00 | 16.33 |
| Example 3.3 | Myristic | 14 | 5.41 | 1.87 | 71.39 | 10.00 | 11.33 |
| Control C | Palmitic | 16 | 6.08 | 1.87 | 71.39 | 0.00 | 20.66 |
| Example 3.4 | Palmitic | 16 | 6.08 | 1.87 | 71.39 | 2.00 | 18.66 |
| Example 3.5 | Palmitic | 16 | 6.08 | 1.87 | 71.39 | 5.00 | 15.66 |
| Example 3.6 | Palmitic | 16 | 6.08 | 1.87 | 71.39 | 10.00 | 10.66 |
| Control D | Stearic | 18 | 6.74 | 1.87 | 71.39 | 0.00 | 20.00 |
| Example 3.7 | Stearic | 18 | 6.74 | 1.87 | 71.39 | 2.00 | 18.00 |
| Example 3.8 | Stearic | 18 | 6.74 | 1.87 | 71.39 | 5.00 | 15.00 |
| Example 3.9 | Stearic | 18 | 6.74 | 1.87 | 71.39 | 10.00 | 10.00 |
| Control E | Behenic | 22 | 8.07 | 1.87 | 71.39 | 0.00 | 18.67 |
| Example 3.10 | Behenic | 22 | 8.07 | 1.87 | 71.39 | 2.00 | 16.67 |
| Example 3.11 | Behenic | 22 | 8.07 | 1.87 | 71.39 | 5.00 | 13.67 |
| Example 3.12 | Behenic | 22 | 8.07 | 1.87 | 71.39 | 10.00 | 8.67 |

The permeation coefficient of a filter treated with the antiperspirant/deodorant compositions of Table 5 were used to determine the resistance of product films to hydrostatic pressure that would be experienced at the outlet of a sweat duct, using the procedure described above. The results are summarized in Table 6.

TABLE 6

Antiperspirant/Deodorant film properties when ZnO was post added or premixed in fatty acid/propylene glycol base

| Sample | Fatty Acid | Carbon Number | weight % ZnO | Permeation Coefficient Ko, NaCl, n (microdarcy) |
|---|---|---|---|---|
| Control B.1 | Myristic | 14 | 0 | 0.0507 |
| Example 3.1 | Myristic | 14 | 2 | 0.2432 |
| Example 3.2 | Myristic | 14 | 5 | 0.1696 |
| Example 3.3 | Myristic | 14 | 10 | 0.155 |
| Control B.2 | Palmitic | 16 | 0 | 0.0004 |
| Example 3.4 | Palmitic | 16 | 2 | -0.004 |
| Example 3.5 | Palmitic | 16 | 5 | 0.0847 |
| Example 3.6 | Palmitic | 16 | 10 | 0.1068 |
| Control B.3 | Stearic | 18 | 0 | 0.0281 |
| Example 3.7 | Stearic | 18 | 2 | 0.017 |

TABLE 6-continued

Antiperspirant/Deodorant film properties when ZnO was post added or premixed in fatty acid/propylene glycol base

| Sample | Fatty Acid | Carbon Number | weight % ZnO | Permeation Coefficient Ko, NaCl, n (microdarcy) |
|---|---|---|---|---|
| Example 3.8 | Stearic | 18 | 5 | 0.017 |
| Example 3.9 | Stearic | 18 | 10 | 0.0565 |
| Control B.4 | Behenic | 22 | 0 | 0.0268 |
| Example 3.10 | Behenic | 22 | 2 | 0.0128 |
| Example 3.11 | Behenic | 22 | 5 | 0.0228 |
| Example 3.12 | Behenic | 22 | 10 | 0.0223 |

As shown in Table 6, the permeation coefficient, water repellancy and film homogeneity were found to depend on both the saturated fatty acid chain length and the amount of ZnO. Furthermore, for the constant amount of zinc oxide, the fatty acids having carbon chain length of greater than 14 (myristic acid) were found to have the more resistance to the hydrostatic pressure, as illustrated by lower value of permeation coefficient observed for the saturated fatty acid chains greater than C14 (myristic acid). In particular, for both stearate and behenate fatty acids, addition of zinc oxide was found to enhance resistance to hydrostatic pressure, by lowering of the permeation co-efficient.

Example 4

Aluminum-Free Antiperspirant/Deodorant Composition Comprising Zinc Oxide and PVM/MA Decadiene Crosspolymer Two antiperspirant/deodorant formulations were prepared using the following procedure of Example 1 for the sample without PVM/MA decadiene crosspolymer, and the following procedure for the sample with PVM/MA decadiene crosspolymer, with compositions shown in Table 7:

Preparation of Solution A: Weighed propylene glycol into a beaker and heated to 75° C. While maintaining the temperature at 75° C., added stearic acid to the propylene glycol with continuous stirring until completely dissolved, followed by dropwise addition of caustic (50% NaOH) while maintaining the temperature constant and continuous stirring until completely dissolved to form a base composition for an antiperspirant/deodorant composition in stick form. After compete dissolution of caustic, zinc oxide particles were dispersed in propylene glycol to form a uniform paste and then this paste was slowly added to the base composition while maintaining the temperature at 75° C. with continuous stirring, until the zinc oxide particles were completely dispersed. Added water, while maintaining the temperature of the formulation at 75° C. with continuous stirring. Once water is completely dissolved, turned off the heat to allow the solution A to cool off to approximately 60° C., while adjusting the mixing speed as necessary.

Preparation of Solution B: Weighed propylene glycol into another beaker and added appropriate amount of PVM/MA decadiene crosspolymer and stirred the solution for a minimum of 2 hours at room temperature.

Prepared a 50/50 mixture of Solution A and Solution B and heated to 80° C. until homogeneous solution is obtained and let it cool. Transferred the antiperspirant/deodorant formulation into a labeled sample collection jar and periodically shaking the jar for approximately 15-30 seconds to insure uniformity within the sample to prevent precipitation of zinc oxide particles, as the cooling process continued and until the sample solidified.

TABLE 7

Compositions with and without PVM/MA decadiene crosspolymer

| Ingredients | Example 4.1 | Example 4.2 |
|---|---|---|
| PVM/MA decadiene crosspolymer | 0.00 | 2.66 |
| Zinc Oxide | 10.00 | 10.00 |
| Stearic Acid | 6.74 | 6.74 |
| 38.8% NaOH in $H_2O$ | 1.87 | 1.87 |
| Deionized $H_2O$ | 17.68 | 17.68 |
| Propylene Glycol | 63.71 | 61.06 |

Hydrostatic pressure of the above two formulations was measured according to the procedure described above and the results are summarized below:

TABLE 8

Resistance to Hydrostatic Pressure

| | Permeation Coefficient Ko, NaCl, n (microdarcy) | P≤ |
|---|---|---|
| Example 4.1 | 0.117 | 0.001 |
| Example 4.2 | 0.032 | 0.001 |

Table 8 shows that the permeation coefficient of the filter treated with formulation of Example 4.2 comprising 2.66 weight % of PVM/MA decadiene crosspolymer is about four times lower than that of Example 4.1, without the PVM/MA decadiene crosspolymer. Thus, the addition of PVM/MA decadiene crosspolymer to an antiperspirant/deodorant composition comprising zinc oxide significantly improves the resistance of the formulation to hydrostatic pressure. Without wishing to be bound by theory, it is believed that an increase in aggregate adhesion and also resistance to hydrostatic pressure due to the presence of PVM/MA decadiene crosspolymer along with zinc oxide, would result in an improvement in antiperspirant benefits due to the enhanced resistance to hydrostatic pressure that may be present in the sweat ducts.

Figure 3A:
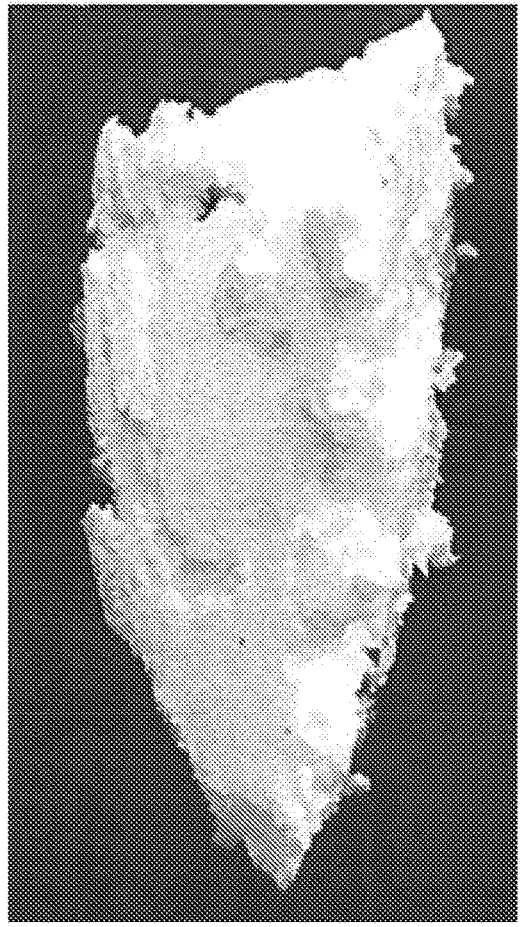
FIG. 3A is an photograph of an antiperspirant/deodorant composition of the present disclosure comprising 10 weight % zinc oxide, but free of PVM/MA decadiene crosspolymer.
Figure 3B:
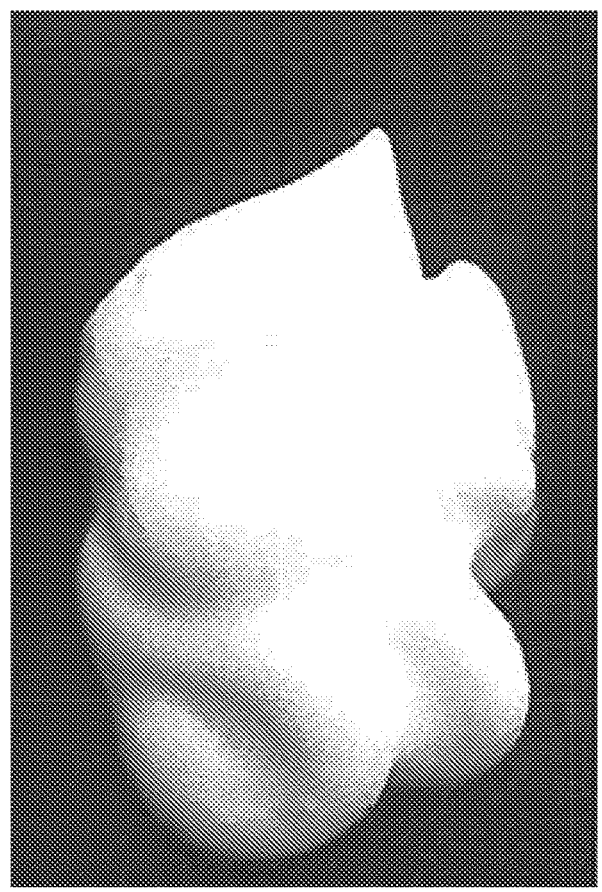
FIG. 3B is an photograph of an antiperspirant/deodorant composition of the present disclosure comprising 10 weight % zinc oxide and a PVM/MA decadiene crosspolymer.

Furthermore, as shown in FIGS. 3A and 3B, it was found that incorporation of PVM/MA decadiene crosspolymer in the antiperspirant/deodorant formulations comprising zinc oxide can significantly reduce gel hardness as shown in FIG. 3A of the Comparative Example B, resulting in a flowable cream formula, as shown in FIG. 3B of the Example 3. Without wishing to be bound by theory, it is speculated that addition zinc oxide to a sodium stearate based gel in the presence of water results in the formation of zinc stearate salts and zinc oxide/stearate aggregates, which in turn can disrupt and modify the normal structure and rheology of stearate based antiperspirant/deodorant sticks, resulting in hardening of the gel and potential loss of stability with time. Hence, PVM/MA decadiene crosspolymer when added to an antiperspirant/deodorant composition comprising zinc oxide not only results in enhanced antiperspirant effect, but also in the product's overall quality.

Example 5

Aluminum-Free Antiperspirant/Deodorant Composition Comprising Zinc Oxide and PVM/MA Decadiene Crosspolymer Four antiperspirant/deodorant formulations were prepared using procedure of Example 4 except that 1 weight % of PVM/MA decadiene crosspolymer was added in all of them, but amounts of zinc oxide and sodium stearate (stearic acid and sodium hydroxide) were varied, with composition as shown in Table 9 below:

TABLE 9

Permeation Coefficient as a function of the amount of zinc oxide and sodium stearate

| | | Comparative Example B | Comparative Example C | Comparative Example D | Example 5 |
|---|---|---|---|---|---|
| Amount in weight % | PVM/MA decadiene crosspolymer | 1 | 1 | 1 | 1 |
| | Zinc Oxide | 0 | 10 | 0 | 10 |
| | Stearic Acid | 0 | 0 | 6.74 | 6.74 |
| | 38.8% NaOH | 0 | 0 | 1.87 | 1.87 |
| | Propylene Glycol | 99 | 89 | 90.39 | 80.39 |
| Permeation Coefficient Ko, NaCl, n (microdarcy) | Mean Ko | 0.333 | 0.358 | 0.229 | 0.073 |
| | Lower 95% | 0.275 | 0.3 | 0.171 | 0.014 |
| | Upper 95% | 0.392 | 0.417 | 0.287 | 0.131 |
| % reduction in permeation coefficient in comparison to the composition of Comparative Example C | | — | -8% | 31% | 78.1% |

Table 9 shows that significant reduction (more than 50%) in the permeation coefficient was obtained when PVM/MA decadiene crosspolymer was incorporated along with zinc oxide and sodium stearate, as shown by Example 5. When either sodium stearate or zinc oxide were present along with PVM/MA decadiene crosspolymer, the reduction in permeation coefficient was either absent (Comparative example C) or minimal (Comparative Example D). It should be appreciated that the stearic acid may be pure stearic acid or a commercial product including primarily stearic acid in a mixture with other minor fatty acids.

Example 6: Permeation Coefficient as a Function of Zinc Oxide and PVM/MA Decadiene Crosspolymer Same procedure as used in Example 4 was used to make various antiperspirant/deodorant compositions as shown in Table 11. Permeation coefficient was then determined for these antiperspirant/deodorant compositions using the procedure described above. The antiperspirant/deodorant compositions and the permeation results are also summarized in Table 11.

TABLE 11

|  | Amount in weight % | | | | Permeation Coefficient $K_{o,NaCl,n}$ (microdarcy) | | |
| --- | --- | --- | --- | --- | --- | --- | --- |
| Sample # | Propylene Glycol | Stearic Acid | Caustic (50% NaOH) | Zinc oxide | PVM/MA decadiene crosspolymer | Mean | Lower 95% | Upper 95% |
| Comparative Example E.1 | 91.39 | 6.74 | 1.87 | 0 | 0 | 0.0042 | −0.0228 | 0.0313 |
| Comparative Example E.2 | 90.39 | 6.74 | 1.87 | 0 | 1 | 0.1127 | 0.0857 | 0.1397 |
| Comparative Example E.3 | 88.39 | 6.74 | 1.87 | 0 | 3 | 0.3864 | 0.3594 | 0.4134 |
| Comparative Example E.4 | 86.39 | 6.74 | 1.87 | 5 | 0 | 0.0065 | −0.0205 | 0.0335 |
| Example 6.1 | 85.39 | 6.74 | 1.87 | 5 | 1 | 0.0209 | −0.0061 | 0.048 |
| Example 6.2 | 83.39 | 6.74 | 1.87 | 5 | 3 | 0.0258 | −0.0012 | 0.0528 |
| Comparative Example E.5 | 81.39 | 6.74 | 1.87 | 10 | 0 | 0.0294 | 0.0024 | 0.0564 |
| Example 6.3 | 80.39 | 6.74 | 1.87 | 10 | 1 | 0.0121 | −0.0149 | 0.0391 |
| Example 6.4 | 78.39 | 6.74 | 1.87 | 10 | 3 | 0.0081 | −0.0189 | 0.0351 |

Table 11 shows that the most significant decrease in permeation coefficient upon addition of PVM/MA decadiene crosspolymer to the antiperspirant/deodorant compositions comprising zinc oxide was observed when the amount of zinc oxide was greater than or equal to about 5 weight %. Furthermore, comparing Comparative Examples E.1, E.2, and E.3, it clearly shows that the addition of PVM/MA decadiene crosspolymer to the antiperspirant/deodorant compositions comprising no zinc oxide is detrimental, as shown by an increase in permeation coefficient with an increase in the amount of PVM/MA decadiene crosspolymer. This is in alignment with observations made in Example 4 that for optimum antiperspirant efficacy, zinc oxide, PVM/MA decadiene crosspolymer and sodium stearate need to be present together.

Example 7: Reduction in White Residue

Two antiperspirant/deodorant formulations were prepared using procedure of Example 4 except that PVM/MA decadiene crosspolymer was added in one, with composition as shown in Table 10 below.

White residue analysis was done by depositing 50 mg of each of the composition—Example 7.1 and Example 7.2—on human skin on adjacent sites on a hand. The formulations were rubbed into the skin for the same number of strokes for 10 seconds at the same time. The results are summarized in Table 10 and FIG. 4.

TABLE 10

Compositions for White Residue Analysis

| | Ingredients | Example 7.1 | Example 7.2 |
| --- | --- | --- | --- |
| Amount in weight % | PVM/MA decadiene crosspolymer | 0 | 1 |
| | Zinc Oxide | 10 | 10 |
| | Stearic Acid | 6.74 | 6.74 |
| | 38.8% NaOH in H$_2$O | 1.87 | 1.87 |
| | Propylene Glycol | 81.39 | 80.39 |
| White Residue | "White" Pixel Count | 4551 | 756 |

TABLE 10-continued

Compositions for White Residue Analysis

| | Ingredients | Example 7.1 | Example 7.2 |
| --- | --- | --- | --- |
| Analysis | % Total Reduction in "White" Pixel Count relative to Example 7.1 | | 83.4 |

As shown in the Table 10, addition of ZnO to a sodium stearate based gel (Example 7.1) results in visible residue. Without wishing to be bound by theory, it is believed that the visible residue could be from zinc oxide, zinc stearate, and zinc oxide/stearate aggregates. However, as shown by Example 7.2, addition of PVM/MA decadiene crosspolymer results in a substantial decrease (more than 90%) in the visible white residue. It is evident from FIGS. 4A and 4B that addition of the PVM/MA decadiene crosspolymer reduces the visible white residue due to the ZnO and stearate present in the formulation.

Histogram segmentation analysis of FIG. 4A, showed about a 6 fold reduction in the amount of "white residue" with incorporation of PVM/MA decadiene crosspolymer. Normal rubbing does not lead to any further reduction of white residue for the ZnO-stearate gel which does not contain PVM/MA decadiene crosspolymer.

Example 8: Permeation Coefficient as a Function of Zinc Oxide and Acyl Substituted Polyvinylpyrrolidone (PVP)

Various antiperspirant/deodorant compositions were made with different acyl substituted polyvinylpyrrolidone (PVP), having different acyl chain length, and varying amounts of zinc oxide using the procedure described in Example 4, except that various acyl substituted polyvinylpyrrolidone (PVP) polymers were used instead of PVM/MA decadiene crosspolymer.

Triacontanyl PVP having an acyl chain length of 30 carbon atoms, VP/Eicosene Copolymer having an acyl chain length of 20 carbon atoms, VP/Hexadecene Copolymer having an acyl chain length of 16 carbon atoms, VP/Hexadecene Copolymer, Octyldodecanol, having a mixture of two different alkyl chain lengths with an estimated average acyl chain length of 19 carbon atoms were used. Table 12 summarizes the composition and Table 13 summarizes the results of permeation coefficient measured using the procedure disclosed hereinabove.

TABLE 12

| Ingredient | Amount in weight % |
| --- | --- |
| Stearic acid | 6.74 |
| Caustic (50%) | 1.87 |
| Propylene Glycol | QS |
| Acyl substituted polyvinylpyrrolidone (PVP) (C16-C30) | 1-6 |
| Zinc Oxide | 0-10 |

Table 12 summarizes the results of the permeation coefficient measured using the procedure disclosed hereinabove, using ANOVA least square mean analysis of the permeation coefficient as a function of the amount of acyl substituted PVP polymer, acyl chain length, and the amount of zinc oxide.

TABLE 13

Permeation coefficient of compositions including Acyl substituted polyvinylpyrrolidone

| Acyl substituted polyvinylpyrrolidone | Mean Acyl Chain Length | $p < 0.05$ | Permeation Coefficient $\kappa_{o, NaCl, n}$ (microdarcy) |
| --- | --- | --- | --- |
| VP/Hexadecene Copolymer | 16 | A | 0.010780 |
| VP/Hexadecene Copolymer, Octyldodecanol | mixture | AB | 0.008080 |
| VP/Eicosene Copolymer | 20 | BC | 0.004450 |
| Triacontanyl PVP | 30 | C | 0.002300 |

Table 13 shows that increasing the alkyl chain length appears to decrease the permeation coefficient consistent with an increased resistance to hydrostatic pressure.

Example 9 & Comparative Example F.1-F.14: Effect of the Presence of Magnesium Oxide on the Zinc Substantivity Table 14 shows various antiperspirant/deodorant compositions comprising various amounts of zinc oxide and magnesium oxide and the resulting zinc substantivity. The zinc substantivity data was collect by digesting the pig skin in nitric acid and then quantifying the amount of substantive zinc by flame ionization and then normalizing against the total dried tissue weight.

TABLE 14

Effect of the presence of MgO on zinc substantivity

| Sample | Propylene Glycol | Glycerine | 50% Caustic | Stearic Acid | Potassium Chloride | Water | Zinc Oxide | Magnesium Oxide | Mgo/ZnO Ratio | calculated uM Zn/mg tissue recovered (LSM) | % Reduction in Zn as compared to composition without MgO |
| --- | --- | --- | --- | --- | --- | --- | --- | --- | --- | --- | --- |
| F.1 | 55 | 12 | 1.87 | 6.74 | 1 | Q.S. | 1.5 | 1.25 | 0.83 | 3.883 | — |
| F.2 | 55 | 12 | 1.87 | 6.74 | 1 | Q.S. | 1.5 | 2.5 | 1.67 | 2.542 | — |
| 9.1 | 55 | 12 | 1.87 | 6.74 | 1 | Q.S. | 2 | 0 | 0 | 5.920 | — |
| F.3 | 55 | 12 | 1.87 | 6.74 | 1 | Q.S. | 2 | 1.25 | 0.63 | 4.579 | 23% |
| F.4 | 55 | 12 | 1.87 | 6.74 | 1 | Q.S. | 2 | 2.5 | 1.25 | 3.239 | 45% |
| 9.2 | 55 | 12 | 2.06 | 7.43 | 1 | Q.S. | 2 | 0 | 0 | 5.481 | — |
| F.5 | 55 | 12 | 2.06 | 7.43 | 1 | Q.S. | 2 | 1.25 | 0.63 | 4.159 | 24% |
| F.6 | 55 | 12 | 2.06 | 7.43 | 1 | Q.S. | 2 | 2.5 | 1.25 | 2.800 | 49% |
| F.7 | 67 | 0 | 1.87 | 6.74 | 1 | Q.S. | 1.5 | 1.25 | 0.83 | 4.140 | — |
| F.8 | 67 | 0 | 1.87 | 6.74 | 1 | Q.S. | 1.5 | 2.5 | 1.67 | 2.799 | — |
| 9.3 | 67 | 0 | 1.87 | 6.74 | 1 | Q.S. | 2 | 0 | 0 | 6.177 | — |
| F.9 | 67 | 0 | 1.87 | 6.74 | 1 | Q.S. | 2 | 1.25 | 0.63 | 4.836 | 22% |
| F.10 | 67 | 0 | 1.87 | 6.74 | 1 | Q.S. | 2 | 2.5 | 1.25 | 3.496 | 43% |
| F.11 | 67 | 0 | 2.06 | 7.43 | 1 | Q.S. | 1.5 | 1.25 | 0.83 | 3.701 | — |
| F.12 | 67 | 0 | 2.06 | 7.43 | 1 | Q.S. | 1.5 | 2.5 | 1.67 | 2.360 | — |
| 9.4 | 67 | 0 | 2.06 | 7.43 | 1 | Q.S. | 2 | 0 | 0 | 5.738 | — |
| F.13 | 67 | 0 | 2.06 | 7.43 | 1 | Q.S. | 2 | 1.25 | 0.625 | 4.397 | 23% |
| F.14 | 67 | 0 | 2.06 | 7.43 | 1 | Q.S. | 2 | 2.5 | 1.25 | 3.057 | 47% |

As shown in the Table 14 above, increasing the amount of magnesium oxide in the antiperspirant/deodorant composition comprising zinc oxide decreases the substantivity of zinc. Furthermore, ANOVA analysis also shows that the addition of MgO causes a statistically significant decrease in Zn substantivity. Hence, this clearly shows that it is desirable for an antiperspirant/deodorant composition comprising zinc oxide to be free or essentially/substantially free of magnesium-based actives, such as magnesium oxide and magnesium hydroxide, in order to maintain zinc substantivity.

Example 10: Magnesium and Tin/Stannous Based Antiperspirant/Deodorant Compositions Non-zinc based antiperspirant/deodorant compositions were evaluated. Particularly, a magnesium-based antiperspirant/deodorant composition (10.1) and a tin-based antiperspirant/deodorant composition (10.2) were prepared by combining the components ingredients of Table 15.

TABLE 15

Antiperspirant/Deodorant Composition:

| Aluminum-free Antiperspirant/ deodorant composition | Example (Amounts in weight %) | |
|---|---|---|
| | 10.1 | 10.2 |
| Magnesium (Magnesium Oxide) | 0.54 | — |
| Tin (Tin (II) Chloride Dihydrate) | — | 2.56 |
| Propylene Glycol USP | 70.52 | 68.5 |
| Demineralized Water | 17.68 | 17.68 |
| Stearic Acid - Triple Pressed Grade | 6.74 | 6.74 |
| Membrane Cell Caustic - 50% NaOH | 1.87 | 1.87 |
| PVM/MA Decadiene Crosspolymer | 2.65 | 2.65 |

The antiperspirant/deodorant formulations of Example 10.1 and 10.2 were tested for antiperspirant efficacy using the starch/iodine test, the results of which are summarized below in Table 16.

TABLE 16

Antiperspirant Efficacy

| | Example | |
|---|---|---|
| | 10.1 | 10.2 |
| % Sweat Reduction | 30.0 | 39.8 |
| Permeation Coefficient (µDarceys) | 0.0517 | 0.0301 |
| Metal Concentration | 0.134 | 0.113 |
| % SR/M | 2223.9 | 352.2 |
| uD/M | 0.39 | 0.27 |
| % SR*M | 4.02 | 4.50 |
| uD*M | 0.00693 | 0.00340 |

The present disclosure has been described with reference to exemplary implementations. Although a limited number of implementations have been shown and described, it will be appreciated by those skilled in the art that changes may be made in these implementations without departing from the principles and spirit of the preceding detailed description. It is intended that the present disclosure be construed as including all such modifications and alterations insofar as they come within the scope of the appended claims or the equivalents thereof.

What is claimed is:

1. An antiperspirant/deodorant composition comprising:
    a) a base composition comprising:
        a. a carrier comprising a polyhydric alcohol or a mixture of a polyhydric alcohol and water, wherein the polyhydric alcohol comprises an organic compound containing 2 to 6 carbon atoms and 2 to 6 hydroxy groups;
        b. a thickening agent comprising a $C_{14-22}$ fatty acid salt, wherein the $C_{14-22}$ fatty acid salt comprises at least one of an alkali metal, an alkaline earth metal, a transition metal, or an amine salt of $C_{14-22}$ fatty acid;
    b) an antiperspirant active and a film-forming polymer dispersed in the base composition,
        wherein the antiperspirant active consists essentially of a zinc-based antiperspirant active, and
        wherein the antiperspirant/deodorant composition is essentially free of magnesium-based actives.

2. The antiperspirant/deodorant composition of claim 1, wherein the zinc-based antiperspirant active comprises one or more of zinc oxide, zinc hydroxide, zinc hydroxide ions, and zinc ions.

3. The antiperspirant/deodorant composition of claim 1, wherein the antiperspirant/deodorant composition is essentially free of aluminum-based antiperspirant actives.

4. The antiperspirant/deodorant composition of claim 1, wherein the zinc-based antiperspirant active comprises zinc oxide present in an amount of from 0.5 to 10 weight %, based on the total amount of the antiperspirant/deodorant composition.

5. The antiperspirant/deodorant composition of claim 1, wherein the film-forming polymer comprises at least one of a copolymer of maleic anhydride and methyl vinyl ether crosslinked with 1,9-decadiene, a mixture of polyester-10 and propylene glycol dibenzoate; a mixture of polyester-7 and neopentyl glycol diheptanoate; adipic acid/diglycol crosspolymer; trimethylpentanediol/adipic acid/glycerin crosspolymer; trimethylpentanediol/adipic acid copolymer; capryloyl glycerin/sebacic acid copolymer; and an acyl substituted polyvinylpyrrolidone having an average acyl chain length of 16 to 30 carbon atoms.

6. The antiperspirant/deodorant composition of claim 1, wherein the film forming polymer comprises a Copolymer of maleic anhydride and methyl vinyl ether crosslinked with 1,9-decadiene, present in an amount of 0.1 to 5 weight %, based on the total weight of the antiperspirant/deodorant composition.

7. The antiperspirant/deodorant composition of claim 1, wherein the $C_{14-22}$ fatty acid salt comprises at least one of myristic, palmitic, stearic, behenic, oleic, linoleic, and linolenic acid, and one or more of sodium, potassium, calcium, magnesium, diethylamine, triethyl amine as a counterion.

8. The antiperspirant/deodorant composition of claim 1, wherein the $C_{14-22}$ fatty acid salt comprises a completely or a partially neutralized stearic acid.

9. The antiperspirant/deodorant composition of claim 1, wherein the $C_{14-22}$ fatty acid salt is present in an amount of 0.5 to 8 weight %, based on the total weight of the antiperspirant/deodorant composition.

10. The antiperspirant/deodorant composition of claim 1, wherein the polyhydric alcohol is propylene glycol.

11. The antiperspirant/deodorant composition of claim 1, wherein the polyhydric alcohol is present in an amount of 65 to 95 weight %, based on the total weight of the antiperspirant/deodorant composition.

12. The antiperspirant/deodorant composition of claim 1, wherein the antiperspirant/deodorant composition is in the form of stick, cream, or flowable gel.

13. A method of reducing apparent perspiration comprising applying the antiperspirant/deodorant composition of claim 1 to an axillary area of a person, wherein the antiperspirant/deodorant composition of claim 1 reduces apparent perspiration.

14. An antiperspirant/deodorant composition comprising:
   a) a base composition comprising:
      (i) a carrier consisting essentially of a polyhydric alcohol or a mixture of a polyhydric alcohol and water, wherein the polyhydric alcohol comprises an organic compound containing 2 to 6 carbon atoms and 2 to 6 hydroxy groups;
      (ii) a thickening agent comprising a $C_{14-22}$ fatty acid salt, wherein the $C_{14-22}$ fatty acid salt comprises at least one of an alkali metal, an alkaline earth metal, a transition metal, or an amine salt of $C_{14-22}$ fatty acid;
   b) an antiperspirant active consisting essentially of a zinc-based antiperspirant active dispersed in the base composition,
      wherein the antiperspirant/deodorant composition is essentially free of aluminum-based antiperspirant actives and magnesium-based actives.

15. The antiperspirant/deodorant composition of claim 14, wherein the antiperspirant/deodorant composition is essentially free of morpholine, pyridine, acetic acid, ethylene carbonate, propylene carbonate, N-methyl pyrrolidone, pyrrolidone, butyrolactone, dimethylsulfoxide, dimethyl formamide, 2-ethoxyethanol, caprolactam.

\* \* \* \* \*